United States Patent [19]

Nowacki et al.

[11] Patent Number: 4,809,692
[45] Date of Patent: Mar. 7, 1989

[54] PEDIATRIC ASTHMATIC MEDICATION INHALER

[75] Inventors: Christopher Nowacki, Arlington Heights; Alfred G. Brisson, Kildeer; Exequiel Dela-Cruz, Arlington Heights, all of Ill.

[73] Assignee: Trudell Medical, London, Canada

[21] Appl. No.: 58,683

[22] Filed: Jun. 4, 1987

Related U.S. Application Data

[63] Continuation of Ser. No. 824,529, Jan. 31, 1986, abandoned.

[51] Int. Cl.$^4$ ............................................. A62B 18/08
[52] U.S. Cl. ............................ 128/206.24; 128/203.29
[58] Field of Search .................. 128/200.23, 200.14, 128/201.11, 203.29, 206.27, 206.24, 206.21, 205.21, 206.26, 206.28, 204.13, 204.14, 205.17, 205.15, 205.17, 716, 719, 725

[56] References Cited

U.S. PATENT DOCUMENTS

| | | | |
|---|---|---|---|
| 2,376,971 | 5/1945 | Kleet | 128/725 |
| 2,848,994 | 8/1958 | Aguado | 128/207.12 |
| 2,931,356 | 4/1960 | Schwarz | 128/206.24 |
| 2,939,958 | 6/1960 | Lundquist | 128/206.21 |
| 3,045,671 | 7/1962 | Updegraff | 128/205.71 |
| 3,918,448 | 11/1975 | McCosker | 128/206.24 |
| 4,296,796 | 10/1981 | Mason, Jr. et al. | 128/206.24 |
| 4,484,577 | 11/1984 | Sackner et al. | 128/203.29 |
| 4,534,343 | 8/1985 | Nowacki et al. | 128/200.23 |
| 4,579,826 | 4/1986 | Bolton et al. | 128/719 |

FOREIGN PATENT DOCUMENTS

| | | | |
|---|---|---|---|
| 1806129 | 9/1969 | Fed. Rep. of Germany | 128/206.24 |
| 14924 | 8/1892 | United Kingdom | 128/203.29 |
| 920216 | 3/1963 | United Kingdom | 128/206.24 |
| 1060664 | 3/1967 | United Kingdom | 128/205.13 |

Primary Examiner—Edward M. Coven
Assistant Examiner—K. M. Reichle
Attorney, Agent, or Firm—Robert M. Wolters

[57] ABSTRACT

A pediatric medication inhaler is provided having an entering end and an exit end. A commercial medication dispenser is secured in the entering end, and a one-way valve is incorporated between the entering end and the exit end permitting air and medication flow from the entering end to the exit end, but preventing flow in the opposite direction. An adapter is secured to the exit end and is made of pliable foam plastic material contoured and adapted to conform to an infant's face. A whistle is provided in the adapter to provide an audible signal that the infant is breathing properly.

8 Claims, 1 Drawing Sheet

U.S. Patent  Mar. 7, 1989  4,809,692
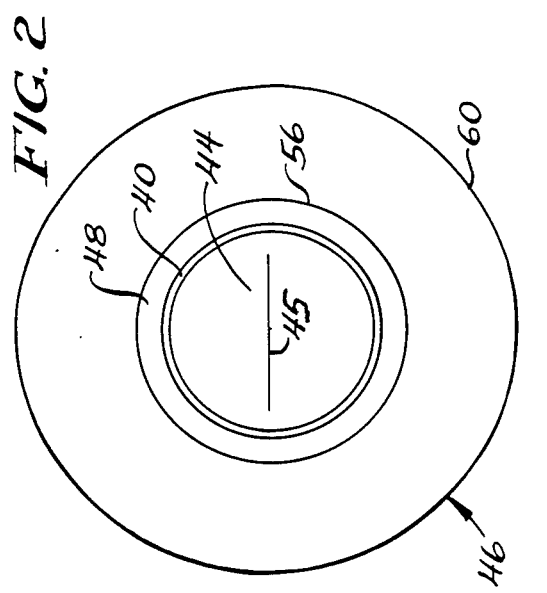
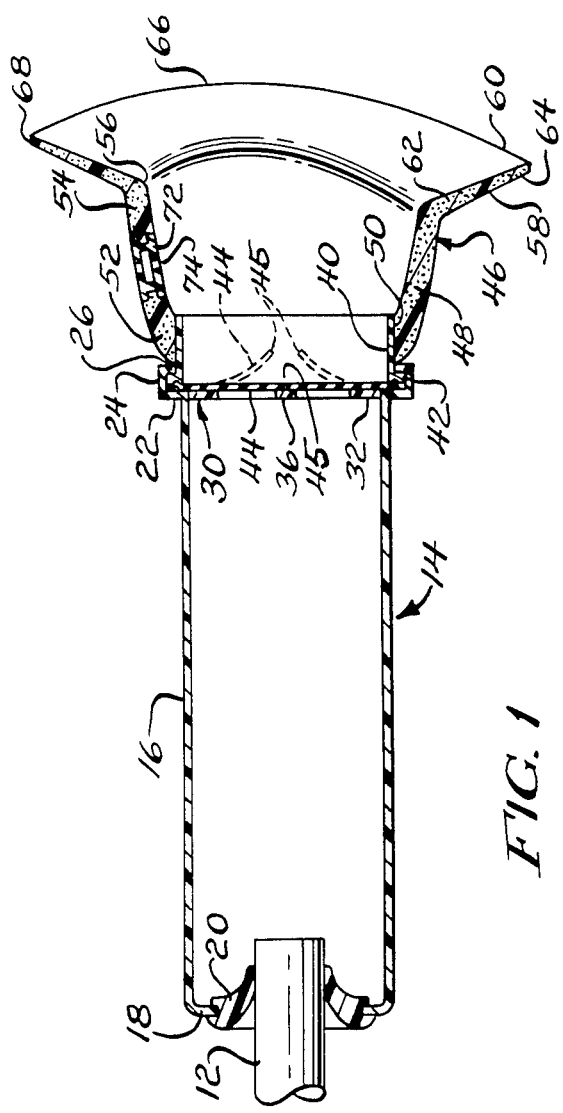
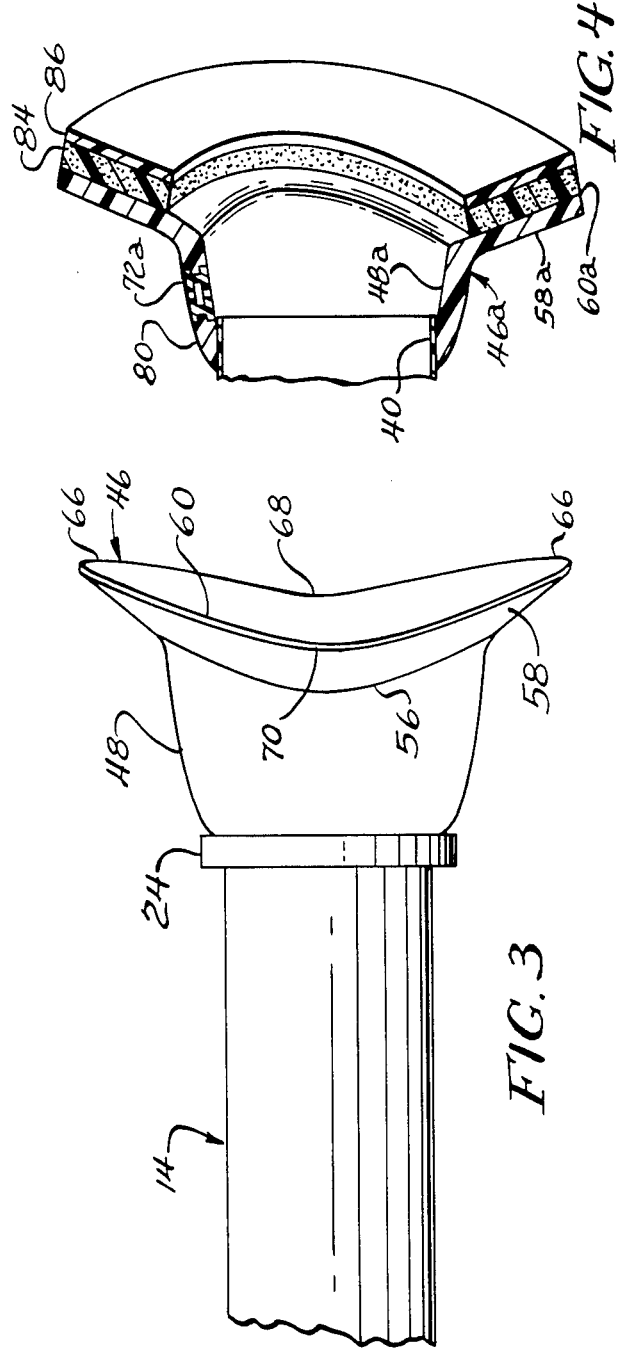
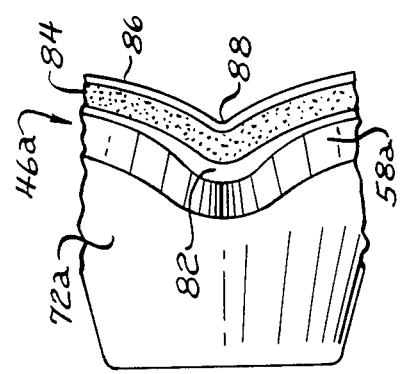

PEDIATRIC ASTHMATIC MEDICATION INHALER

This application is a continuation of application Ser. No. 824,529, filed Jan. 31, 1986, now abandoned.

BACKGROUND OF THE INVENTION

A person suffering from asthma may have rather considerable trouble in beathing when suffering from an asthmatic attack, due to swelling in the bronchii and due to secretion of mucous. There are various anti-asthmatic pills that are effective, but which generally are somewhat slow-acting. There are also medications available for intravenous treatment which work quite rapidly, but which require administration by skilled medical personnel. For most patients the promptest, immediately available relief is by way of an inhalant. Epinephrine or other suitable asthmatic medication is packaged with a suitable diluent in a small pressurized canister or cartridge which interfits with a mouthpiece. The patient places the mouthpiece in his mouth, and depresses the cartridge, thereby releasing a measured amount of medication which is inhaled through the mouthpiece.

Some patients do not inhale properly, and the mouthpiece may not be completely effective in cooperation with the cartridge to convert the medication into a mist which is deposited in the proper bronchial area to relieve the asthmatic attack. Often there are small droplets, rather than a mist, and this may be compounded by improper inhalation which results in much of the medication simply going into the throat and stomach where it is ineffective against the asthmatic attack.

In our prior U.S. Pat. No. 4,470,412 we have disclosed a remarkably efficient and low-cost inhalation valve in the nature of an extended mouthpiece for a bronchodilator which aids the asthmatic sufferer in properly inhaling, and in breaking up droplets into a mist form. This inhalation valve has achieved extensive commercial success.

Our inhalation valve as discussed above is for use by a patient who can take the mouthpiece thereof into his mouth and inhale and exhale through the mouthpiece. Babies or small children cannot be relied upon properly to hold the mouthpiece in the mouth, and indeed the baby's mouth may be too small for the mouthpiece. Furthermore, it cannot be ascertained with certainty under some conditions whether a baby or small child is properly inhaling and exhaling.

OBJECTS AND SUMMARY OF THE PRESENT INVENTION

It is an object of the present invention to provide a pediatric inhalation valve for use by babies and small children which has an adapter thereon fitting over the baby's mouth and nose and sealing to the face, whereby breathing by the baby effects proper inhalation and exhalation through the valve.

It is a further object of the present invention to provide such a pediatric inhalation valve in which a sound is generated upon inhalation and exhalation so that a party applying the inhalation valve and medication to a baby may be sure that the medication is being breathed in.

In accordance with the present invention, we have provided an inhalation valve identical in most respects to that disclosed in our prior U.S. Pat. No. 4,470,412, with the addition of a molded rubber or plastic adapter or face mask which fits over the nose and mouth of a baby or small child. The adapter is molded of foam plastic or rubber material, and the portion thereof adjacent to the inhalation valve is relatively thick to provide a degree of rigidity thereto. However, the outer portion of the adapter that fits against the face of the infant tapers to a thinner wall section, whereby it is considerably more flexible and adaptable, and also comfortable to the user.

THE DRAWINGS

The invention will best be understood with reference to the following text when taken in connection with the accompanying drawings wherein:

FIG. 1 is a longitudinal sectional view illustrating our pediatric inhalation valve forming the subject matter of the present invention;

FIG. 2 is a right-end view thereof;

FIG. 3 is a bottom view thereof;

FIG. 4 is a fragmentary axial sectional view similar to a part of FIG. 1 and showing a modification of the invention; and FIG. 5 is a fragmentary top view of the embodiment of FIG. 4.

DETAILED DISCLOSURE OF THE ILLUSTRATED EMBODIMENT

As is well known, and as is summarized in our prior U.S. Pat. No. 4,470,412, a small pressurized canister or cartridge, sometimes referred to as a nebulizer, is charged with epinephrine or other suitable anti-asthmatic medication in a suitable diluent, and under pressure. The cartridge fits into a receiving end of a right angle mouthpiece, the opposite end of which is placed in the asthmatic sufferer's mouth. The cartridge is pressed down, being squeezed between the index finger and thumb underlying the mouthpiece. This causes a valve stem in the cartridge to press against the reaction base in the mouthpiece to discharge a measured quantity of medication into the mouthpiece. The discharge is supposed to be in the form of a mist, but in fact often contains small droplets. The patient inhales, and the mist passes into the mouth, and hopefully into the bronchial tubes to provide asthmatic relief. The patient is then supposed to hold his breath for a short time, and subsequently to inhale slowly through nearly closed lips. However, as noted heretofore, some of the medication may simply be in the form of droplets rather than mist, and the droplets generally are simply swallowed and do not reach the bronchial tubes to effect their intended purpose.

As is disclosed in detail in our aforesaid prior patent, we have found that the drops can be broken up into a mist and the patient can be more or less forced to inhale properly through the use of a inhalation valve forming the subject of our prior U.S. Pat. No. 4,470,412. This inhalation valve is shown herein in somewhat less detail, but sufficient for an understanding in combination with a pediatric adapter or face mask.

With reference first to FIG. 1, there is shown an inhalation valve 14 comprising a cylinder 16 preferably molded of a suitable plastic material. The cylinder is provided at its entering end (the left end in FIG. 1) with a radially inwardly directly flange 18 of limited extent. This flange retains a generally frustoconical elastomeric adapter 20 which receives the exit end of the right angle mouthpiece 12. The frustoconical shape and the elastomeric nature of the adapter 20 are such that mouthpieces of widely different sizes and configurations can be gripped securely.

At the opposite end of the cylinder 16 there is an outwardly extending peripheral flange 22 having at its extremity an axially extending cylindrical flange 24. At its extremity the cylindrical flange 24 is provided with an inwardly directed flange 26 which is interrupted at arcuately spaced locations for bayoneting of teeth of a part subsequently to be described therewith.

Inwardly of the flange 22 and at the exit end of the cylinder there is a spider 30. The spider may be molded integrately with the cylinder 16, but more conveniently is a separate plastic piece which is secured within the cylinder by way of known techniques such as cementing, sonic welding, etc. The spider comprises an annular ring 32 having formed therewith a plurality of radial ribs joined together at the center at 36. By way of example in our prior U.S. Pat. No. 4,470,412 there are eight such ribs, but the precise number is not critical. There should, however, be one pair of ribs extending diametrically across the spider in a horizontal direction as the parts are oriented in FIG. 1.

Further structure at the exit or right end of the cylinder 14 is similar to that in our prior U.S. Pat. No. 4,470,412, but differs in detail therefrom. A somewhat elongated cylinder 40 is of proper diameter to fit just within the inner edge of the flange 26, and has a radially extending flange 42 which is interrupted thereby defining teeth to permit axial assembly past the flange 26, with rotation from the assembling position securing the cylinder 40 and flange 42 in place.

A resinous plastic or elastomeric diaphram 44 lies immediately to the right of the spider 30 and has its outer periphery trapped between the flange 22 and the flange 42. The diaphram is imperforate except for a horizontal slit 45 extending across the horizontal radial ribs connected to the center 36. Thus, when there is any air pressure to the left from the exit end of the valve 14 the diaphram is pushed firmly against the spider 30, and substantially no air flow is permitted to the left. However, upon inhalation, the pressure is from left to right, and the diaphram deflects away from the spider as indicated in broken lines in FIG. 1, opening the slit to a fairly wide aperture 45 and permitting air flow (and medication flow) therethrough.

The pediatric inhalation valve of the present invention is completed by an adapter or fitting 46 in the nature of a face mask. The adapter 46 is molded of a resiliant foam material, such as closed cell foam rubber or closed cell foam plastic, and includes an inner section 48 of generally frustoconical shape and shallow angle. At its inner extremity the portion 48 has a cylindrical surface 50 which snuggly engages the outer surface of the cylinder 40. The wall of the frustoconical portion 48 is relatively thick at 52 at the inner end thereof, and thins out to a thinner section 54 adjacent the outer margin thereof. At the outer margin 56 the fitting 46 flares outwardly at a wider angle forming a flange 58 extending to the periphery 60 of the fitting. The wall of the flange is thickest at 62 adjacent the extremity 56 which is in the nature of a knee or inflection, although somewhat thinner than the wall at 54, and tapers to a relatively thin section 64 adjacent the periphery 60. As may be seen in FIG. 2 the periphery 60 is circular in outline as is the knee 56. However, neither is a true circle, since they do not lie in planes, but rather are shaped as shown in FIG. 3. Specifically, and is shown also in FIG. 1, the periphery of the flange 58 extends further to the right somewhat above the center line as indicated at 66, and then indents to the left at 68 in the top portion on a vertical median plane. It tapers to the left also below the extreme extension at 66 to an indentation 70 to a greater degree than the indentation 68. The periphery 60 of the adapter thus will fit above the nose in engagement with the face and down along the cheeks to the chin, the indentation 68 engaging approximately at the bridge of the nose, and the indentation 70 engaging the chin.

The adapter is completed by the provision of a whistle 72 incorporated in an aperture in the upper portion of the body 48 along the vertical median plane. This whistle is of a type frequently used in children's squeezed toys, and will emit a whistling sound when air is expelled through it. The whistle may incorporate a one-way valve mechanism so as not to pass air upon inhalation, although this is not critical since it would provide only a small amount of bypass air that would not hurt anything. The whistle has a central bore 74 which serves as the outlet valve upon exhalation, and upon exhalation makes an audible whistling sound so that the person administering asthmatic medication to the infant will know that the infant is exhaling. A certain amount of noise may be generated by the whistle upon inhalation, and this is moderately beneficial although not essential.

The pediatric inhalation valve as heretofore shown as described will be understood as incorporating an inhalation valve generally similar to that disclosed in our prior U.S. Pat. No. 4,470,412, plus the foam adapter described. The adapter, being thin in its outer portions, is readily adaptable to the contours of an individual infant's face, and is comfortable to the infant, and therefore nonthreatening. In fact, if the infant is not too frightened from the asthmatic attack, he may derive some pleasure from the whistling of the whistle upon exhalation.

The adapter may be discarded in moving from one patient to another or it may be washed and reused.

A modification of the adapter of the present invention is shown in FIGS. 4 and 5, wherein similar parts are identified by like numerals with the addition of the suffix a. In this case the adapter is somewhat in the nature of a sandwich, including a base 80 having a body 48a of narrow taper fitting over the cylindrical flange 40 and flaring outwardly at 58a to the outer periphery 60a. This base is of substantially uniform thickness, and includes a whistle 72a similar to the one previously described. The base 80 is of a foam elastomeric or preferably plastic construction, and like the adapter 46 is of a closed cell type to avoid absorption of moisture.

At its upper portion as seen best in FIG. 5 the more widely flared portion 58a is provided with a forwardly extending indentation or offset portion 82 in order best to accommodate an infant's nose.

The base portion is made of a flexible but relatively stiff foam plastic material. A much softer foam ring 84 is secured to the inner or concave surface of the outwardly flared portion 58a by any suitable means such as an adhesive. The ring 84 conforms closely to the shape of the outwardly flared portion 58a. This ring is also made of a foam plastic, but of a much softer nature for better conformability to the infant's face. This foam ring 84 also is of a closed-cell nature, and preferably is a foam plastic, although it could be an elastomeric substance.

Finally, a rather thin ring 86 is secured to the inner or concave surface of the ring 84. This ring is of a closed-cell elastomeric or preferably plastic foam, and is of the type having a surface skin. The surface skin also is preferred on the adapter 46 and on the base portion of adapter 46a. The ring 86 is rather thin and conforms to the shape of the ring 84 and the outwardly flared portion 58a, specifically including a forward projection or indentation 88 aligned with the indentation 82. Since the ring 86 is intended to conform to the infant's face, largely due to the softness of the ring 84, the ring 86 is of a rather thin construction, the important aspect thereof being the surface skin which provides a pleasant touch to the infant's face and which is readily washed with no danger of moisture absorption.

In one specific embodiment of the invention the maximum diameter of the adapter is on the order of 3 to 3½ inches.

The specific examples of an invention as herein shown and described are for illustrative purposes only. Various changes in structure will no doubt occur to those skilled in the art, and will be understood as forming a part of the present invention insofar as they fall within the spirit and scope of the appended claims.

The invention is claimed as follows:

1. A pediatric medication inhaler comprising a body having an entering upstream end and an exit downstream end, means at said entering end for receiving structure for applying inhalation medication, one-way valve means in said body permitting air and medication to flow from said entering end to said exit end and preventing flow from said exit end to said entering end, and a mask-type adapter adapted to conform to an infant's face secured to said exit end having a first substantially frustoconical portion having a flared sidewall with an open base and an open apex with said apex secured in pneumatically sealed relation to said exit end, an integral second substantially frustoconical portion of pliable material coaxial with said first portion and having a flared sidewall and an open base and an open apex, said second portion apex being integral with said first portion base and said second portion sidewall flaring outwardly from said first portion at a greater angle than said first portion flares outwardly from said exit end and said second portion base having an outer annular edge defining said open base, the interior surface of the side wall of said second portion consisting of a frustoconically shaped surface extending from said open apex to said open base and thereby, at least adjacent said outer edge, being adapted to conform to an infant's face when in surface engagement therewith, and signal means mounted in said adapter first portion sidewall for providing a human perceptible signal upon breathing by said infant.

2. An inhaler as set forth in claim 1 wherein said adapter first portion has a sidewall, and wherein said signal means is mounted in said sidewall.

3. An inhaler as set forth in claim 3 wherein said signal means comprises a whistle.

4. An inhaler as set forth in claim 1 wherein said signal means comprises a whistle.

5. An inhaler as set forth in claim 1 wherein said adapter first portion is made of pliable material and is thickest adjacent said exit end and tapers thinner outwardly therefrom for enhanced flexibility.

6. An inhaler as set forth in claim 5 wherein said second portion is thickest adjacent said first portion and tapers thinner outwardly therefrom.

7. An inhaler as set forth in claim 1 wherein said second portion is in the form of a continuous ring, and further including a relatively softer ring on the interior surface thereof adjacent said outer edge adapted to engage an infant's face.

8. An inhaler as set forth in claim 7 and further including a face ring on said relatively softer ring and having an outer surface skin on said face ring adapted to engage an infant's face.

* * * * *